United States Patent
Wang et al.

(10) Patent No.: US 11,819,310 B2
(45) Date of Patent: Nov. 21, 2023

(54) 3-AXIS SIDE-VIEW CONFOCAL FLUORESCENCE ENDOMICROSCOPE

(71) Applicant: THE REGENTS OF THE UNIVERSITY OF MICHIGAN, Ann Arbor, MI (US)

(72) Inventors: Thomas D. Wang, Ann Arbor, MI (US); Xiyu Duan, San Jose, CA (US); Haijun Li, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 799 days.

(21) Appl. No.: 16/633,483

(22) PCT Filed: Jul. 24, 2018

(86) PCT No.: PCT/US2018/043579
§ 371 (c)(1),
(2) Date: Jan. 23, 2020

(87) PCT Pub. No.: WO2019/023287
PCT Pub. Date: Jan. 31, 2019

(65) Prior Publication Data
US 2022/0369933 A1 Nov. 24, 2022

Related U.S. Application Data

(60) Provisional application No. 62/536,285, filed on Jul. 24, 2017.

(51) Int. Cl.
A61B 5/00 (2006.01)
A61B 1/00 (2006.01)
(Continued)

(52) U.S. Cl.
CPC ........ *A61B 5/0068* (2013.01); *A61B 1/00096* (2013.01); *A61B 1/00172* (2013.01);
(Continued)

(58) Field of Classification Search
CPC ................ A61B 5/0068; A61B 5/0071; G02B 21/0028; G02B 21/0048; G02B 21/0076; G02B 23/2461
See application file for complete search history.

(56) References Cited

U.S. PATENT DOCUMENTS 9,389,184 B2 * 7/2016 Wang .................... A61B 1/2733
11,215,805 B2 * 1/2022 Oldham ............... G02B 26/101
(Continued)

OTHER PUBLICATIONS

Duan et al.; "Visualizing epithelial expression of EGFR in vivo with distal scanning side-viewing confocal endomicroscope"; Nature and scientific reports; pp. 1-11 (Year: 2016).*

*Primary Examiner* — Dixomara Vargas
(74) *Attorney, Agent, or Firm* — MARSHALL, GERSTEIN & BORUN LLP

(57) ABSTRACT

An optical probe assembly as a confocal endomicroscope includes an optical focusing stage that focuses an output beam onto a sample and a mirror scanning stage that is movable for scanning the output beam in both a lateral two dimensional plane and an axial direction, using a side-view configuration. The side-view configuration allows for output beam illumination and fluorescent imaging of the sample with greater imaging resolution and improved access to hard to reach tissue within a subject.

15 Claims, 13 Drawing Sheets

(51) Int. Cl.
*A61B 1/04* (2006.01)
*A61B 1/06* (2006.01)
*A61B 1/07* (2006.01)
*G02B 21/00* (2006.01)
*G02B 23/24* (2006.01)

(52) U.S. Cl.
CPC ...... *A61B 1/00177* (2013.01); *A61B 1/00193* (2013.01); *A61B 1/043* (2013.01); *A61B 1/0623* (2013.01); *A61B 1/0638* (2013.01); *A61B 1/07* (2013.01); *A61B 5/0071* (2013.01); *G02B 21/0028* (2013.01); *G02B 21/0048* (2013.01); *G02B 21/0076* (2013.01); *G02B 23/2461* (2013.01)

(56) References Cited

U.S. PATENT DOCUMENTS

2018/0356629 A1* 12/2018 Wang .................... A61B 5/0073
2020/0096753 A1* 3/2020 Oldham .............. G02B 21/0048
2022/0155579 A1* 5/2022 Wang ................. G02B 23/2423
2022/0160232 A1* 5/2022 Wang ................. A61B 1/00126

* cited by examiner

3-AXIS SIDE-VIEW CONFOCAL FLUORESCENCE ENDOMICROSCOPE

CROSS-REFERENCE TO RELATED APPLICATIONS

This application claims the priority benefit under 35 U.S.C. § 119(e) of U.S. Provisional Patent Application No. 62/536,285, entitled, "3-Axis Side-View Confocal Fluorescence Endomicroscope," filed Jul. 24, 2017, the disclosure of which is incorporated herein by reference in its entirety.

STATEMENT OF GOVERNMENTAL INTEREST

This invention was made with government support under Grant No. CA142750 awarded by the National Institutes of Health. The government has certain rights in this invention.

FIELD OF THE DISCLOSURE

The present disclosure generally relates to techniques for imaging tissue using an optical instrument and, more particularly, to techniques for allowing two-dimensional (2D) and three-dimensional (3D) imaging using a side-view optical instrument.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Most internal and external body surfaces are covered with the epithelium, a thin layer of tissue with dimensions of a few hundred microns, that serves as the source of intense biological activity. The epithelium functions as a substrate for electrolyte transport, as well as a source for tissue regeneration. The epithelium also functions as the origin of tumorigenesis.

Because of its many different biological functions, researchers study the epithelium in various ways. Researchers, for example, have genetically engineered mice to express optical reporters that are used to investigate epithelial regulation of transport effects, barrier effects, and proliferation. These studies are usually validated by performing histologies on excised tissue. However, this approach has numerous limitations, including that it provides static information only at finite points in time. Real-time intravital microscopy, by contrast, has been developed to track cell movement over time in an innate host environment. In particular, confocal microscopy has become a powerful method of optical imaging of the epithelium. Confocal microscopy allows for sectioning that penetrates several hundred microns into tissue, which means that an instrument with proper dimensions and geometry can be used repetitively to monitor epithelial processes. Unfortunately, conventional confocal microscopy devices are large and bulky, and require wide surgical exposure that may introduce significant trauma.

Until now, confocal techniques for investigating cellular behavior in the epithelium have been limited by a lack of instruments that can be easily maneuvered and accurately positioned to visualize individual cells. Generally, confocal endomicroscopy employs the use of flexible optical fibers for minimal invasiveness. Current confocal instruments use front-view optics that collect images in the horizontal plane only. Because firm contact with tissue is required to couple light, this orientation limits usefulness in many applications, including when examining the epithelium of small animals. There is a desire for an improved confocal microcopy instrument capable examining the epithelium in a more accurate and more flexible manner.

SUMMARY

The present application describes a handheld optical device that may be used as a microscope system for real-time, three-dimensional (3D) optical imaging. More particularly, the present application describes confocal endomicroscopes with side-view optics that allow the endomicroscopes to be accurately positioned for imaging tissue. The confocal endomicroscopes, configured with the side-view optics, can illuminate a vessel from the side of the endomicroscope, instead of from an end view with conventional devices. The result is that tissue can be imaged using a side illuminating imaging beam. Further, the fluorescence generated by biologic targets in tissue is collected from a side-view, as well. The side view configuration provides for a smaller design without the limitations of tissue access or tissue imaging that can accompany front-view endomicroscopes. As a result of this combined side-illumination and side-viewing, the present techniques offer, for the first time, accurate visualization of individual cells in vivo in small animal epithelium, including, for example, cells that express tdTomato, a fluorophore.

Moreover, confocal endomicroscopes with side-view optics can image in narrower, more confined lumens within a subject, lumens which heretofore were not accessible through endomicroscopic imaging. Epithelial cells, for example, migrate and differentiate in the vertical plane; and a side-view confocal endomicroscope in accordance with teachings herein is able to perform optical sectioning in the vertical direction to study cell function by illuminating and examining tissue from a side-view of an endomicroscope.

In example embodiments, a confocal endomicroscope uses a small, fast 3-axis scanner with side-view optics to collect fluorescence images in either the horizontal or vertical plane to visualize individual cells in vivo, for example.

In accordance with an example, an optical probe scanning assembly comprises: a housing having a proximal end configured to receive an optical fiber beam source and a distal end for positioning at a sample, the housing having a length that extends along a longitudinal axis extending from the proximal end to the distal end; an optical focusing assembly configured to focus an output beam, from the fiber beam source, along an axial beam path; and a mirror scanning assembly positioned downstream of the optical focusing assembly in a post-objective position, the mirror assembly being positioned at an angle relative to the axial beam path to deflect the output beam into a lateral axis for emitting the output beam from a side of the housing, the mirror assembly further configured to rotate along a first axis and a second axis for scanning the output beam along a lateral plane and configured to translate out-of-plane of the first and the second axis for scanning the output beam along an oblique plane.

BRIEF DESCRIPTION OF THE DRAWINGS

For a more complete understanding of the disclosure, reference should be made to the following detailed description and accompanying drawing figures, in which like reference numerals identify like elements in the figures, and in which:

FIG. 5A illustrates a reflectance image collected from grid target shows FOV of 700×600 µm² in the horizontal plane. FIG. 5B illustrates a scan pattern in horizontal plane on flat surface of $L_4$. FIG. 5C illustrates a reflectance image in oblique plane with dimensions of 292 µm of microtrench phantom having a zig-zag pattern with depth of 200 µm. FIG. 5D illustrates a scan pattern of oblique plane projected onto $L_4$. FIG. 5E illustrates a reflectance image of standard resolution target (USAF 1951) in horizontal plane qualitatively shows lateral resolution of <2 µm. Vertical and horizontal bars from group 7, element 6 are clearly seen (inset).

In FIG. 9C liver lobule shows a central vein (arrow) surround by portal triads (t) and perfused by sinusoids (s), and in FIG. 9D kidney shows collecting tubules (arrow) in renal cortex.

DETAILED DESCRIPTION

Figure 1:
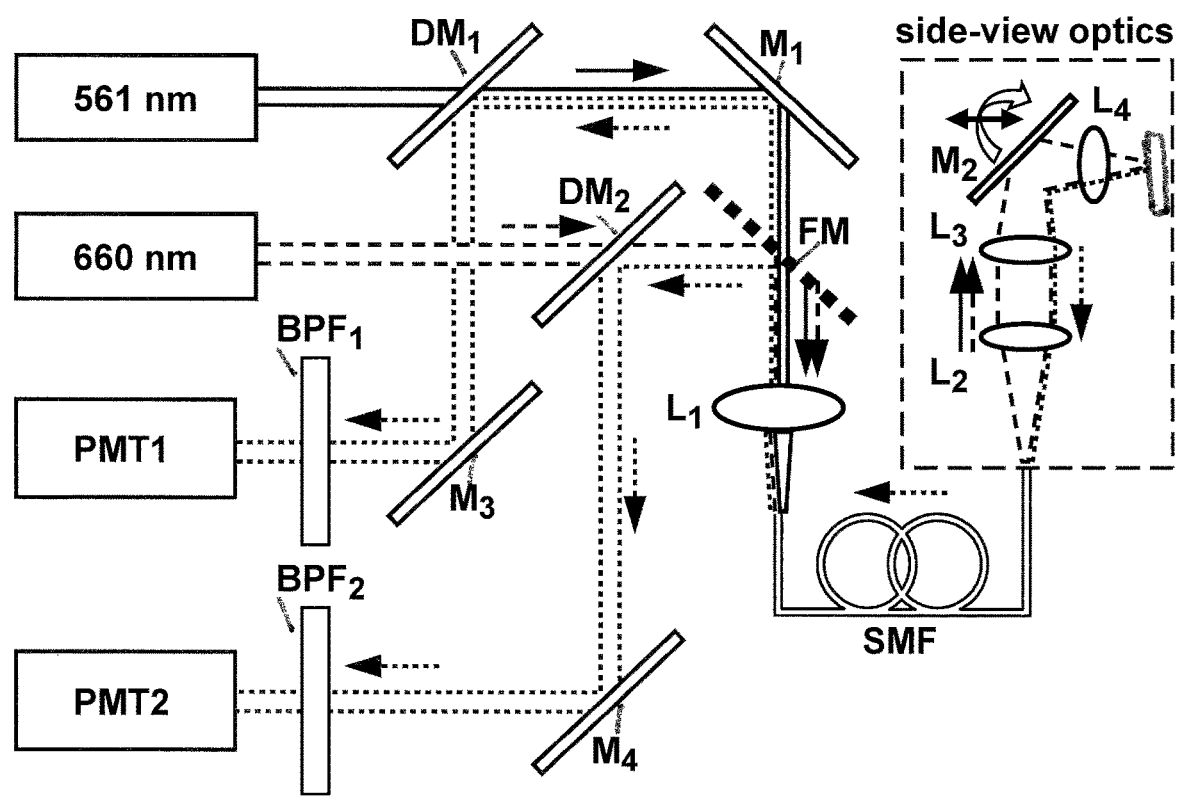
FIG. 1 illustrates a schematic diagram of an example optical probe scanning system, in accordance with an example.

Pursuant to these various embodiments, an optical probe scanning assembly is provided. The optical probe scanning assembly includes a housing having a proximal end configured to receive an optical fiber beam source and a distal end for positioning at a sample. The housing has a length that extends along a longitudinal axis extending from the proximal end to the distal end. An optical focusing assembly is included to focus an output beam, from the fiber beam source, along an axial beam path. Downstream of that optical focusing assembly (where downstream refers a position distal to, or afterwards in the direction of the output beam), is a 3-axis mirror scanning assembly. The mirror assembly is positioned at an angle relative to the axial beam path to deflect the output beam into a lateral axis for emitting the output beam from a side of the housing. For example, the lateral beam path may be orthogonal to the axial beam path for emitting the output beam from a side-view of the optical probe, instead of from a distal end. Further, the mirror assembly may be configured to rotate along a first and a second axes, e.g., x-axis and y-axis, for scanning the output beam along a lateral plane, such as a horizontal plane as defined by the side view. The mirror assembly may be further configured to translate along a third axis for scanning the output beam along an oblique plane.

The present techniques may be implemented in confocal endomicroscopy devices. Confocal endomicroscopy is a minimally invasive imaging technique used to study epithelial biology, e.g., in live animals. With the present techniques we have developed a confocal endomicroscope that has both high numerical aperture (NA) optics and post-objective scanning. The confocal endomicroscope has allowed us to achieve sub-cellular resolution with a large field of view (FOV). With these devices, we have visualized individual colonocytes, goblet cells, and inflammatory cells in vivo from images collected in mouse colonic epithelium. Other imaging methods, including X-ray, ultrasound, computer tomography (CT) and magnetic resonance imaging (MRI), provide structural rather than functional information, and positron emission tomography (PET) does not have adequate speed or resolution to visualize single cells.

In exemplary embodiments, the present techniques use a confocal endomicroscope with side-view operation. In comparison to front-view endoscopic devices, the side-view allows the user rotational and translational maneuverability of the endomicroscope. The user can move the side-view endomicroscope along the axial length of vessel and rotationally about the vessel axis. That means that the user may accurately position the side-view optics on any region of interest (ROI) in the vessel. A user may first identify the ROI, e.g., using wide-field endoscopy, and then image the exact location using the side-view confocal endomicroscope. When trying to image ROI in small vessels, including those found in small animals, front-view devices are cumbersome because adequate contact with the epithelium is difficult to achieve. These endomicroscopes may be small enough to pass into and within the vessel, but the front-end does not contact the tissue that one desires to examine. Moreover, there is no rotation dependent imaging.

Previously, we demonstrated a side-view endomicroscope that utilized a two dimensional (2D) scanner capable of imaging in the horizontal plane, and only at a fixed depth of ~100 µm.

The present techniques, however, provide unexpectedly improved image performance, by using an entirely different configuration, one that deploys a fast, monolithic 3-axis mirror into an endomicroscope. The configuration provides, for the first time, side-view optics capable of scanning in the vertical dimension. Moreover, by adjusting a drive frequency to the endomicroscope, the endomicroscope can controllably "switch" between a tilt mode or a piston mode, i.e., imaging between horizontal and oblique planes. Further still, by placing the scanner in the post-objective position, the excitation beam (which comes from the side) passes on-axis through focusing lenses so that a diffraction-limited spot can be scanned over the lateral dimensions to augment the FOV.

As a result of the present techniques, when imaging, the sensitivity to aberrations is reduced, and, importantly, the endomicroscope can be scaled down in size. For example, in an example arrangement, optimizing the dimensions of multi-beam torsional springs on a scanner element (to increase the mirror deflection angles) allowed us to achieve a FOV of 700×600 µm$^2$, a parameter that is much larger than any previously reported configurations. Further, we have shown imaging resolution below 10 µm, below 5 µm, below 2 µm, and below 1 µm is achievable with scaling of optics and controlling for movement induced effects. These resolutions are attainable in the horizontal and oblique planes, and by virtue of that in the vertical plane as well. In an example arrangement, the confocal endomicroscope achieved a resolution of 1.19 and 3.46 μm in the horizontal and oblique plane, respectively, with either a lateral FOV of 700×600 μm² or a vertical depth of 200 μm. As shown, ROIs can be rapidly identified and electronically magnified by tuning the drive signal to the scanner and highlighting individual cells of interest. As further shown, with example side-view configurations described herein, the focal point can be made to move in both lateral and axial directions to image and in an oblique rather, than a pure vertical plane. The vertical plane can then be extracted from collected 3D volumetric images.

The fast 3-axis beam scanning capability of confocal endomicroscopes described herein provides several technological advances for in vivo imaging of the epithelium. Previously, a side-view microprobe was demonstrated that uses a graded-index (GRIN) lens attached to a prism in a tabletop set-up. Raster scanning was performed using galvos at the proximal end, and the design is was able to achieve a FOV of 250×250 μm² with lateral and axial resolution of 1 and 10 μm, respectively. The objective mechanically rotated to produce a wide map of mouse epithelium, and repetitive imaging of colon was demonstrated. The device was not capable of vertical scanning. Another design, specifically a hand-held, front-view confocal probe based on a resonant fiber demonstrated optical sections in the horizontal plane with depths up to 250 μm. For the front-view confocal probe scanning was performed at the distal end, and a FOV of 475×475 μm² was achieved with lateral and axial resolution of 0.7 and 7 μm, respectively. For example, in vivo imaging of VEGF was performed in the colon of APC$^{min}$ mice using an Alexa-Fluor 488-labeled antibody specific for VEGF. This rigid 5 mm diameter instrument required wide surgical exposure of the abdomen, surgical exposure so wide that it may elicit an injury response from immune mediators. In yet another example, a flexible probe with front-view optics based on a fiber bundle demonstrated optical sections in the horizontal plane at fixed depths ranging between 30-100 μm. Here, scanning was performed at the proximal end with galvos, and a FOV of 160×120 μm² with lateral and axial resolution of 2.5 and 20 μm, respectively, was achieved. The fiber bundle limits image resolution, and separate miniprobes are needed to image in different horizontal planes. All of these conventional confocal probe designs show markedly lower performance than can be achieved with the present techniques.

FIG. 1 illustrates a schematic representation of an imaging system in accordance with an example arrangement, and having the following nomenclature: DM—dichroic mirror, M—mirror, FM—flip mirror, SMF—single mode fiber, L—lens, BPF—band pass filter, PMT—photomultiplier tube. The side-view optics labels an optical probe scanning assembly, in accordance with an example embodiment. As shown in the particular example, fluorescence excitation at $l_{ex}$=561 and 660 nm was provided using two solid-state diode lasers. A visible light beam (e.g., at 561 nm) passes through a dichroic mirror ($DM_1$) and is reflected at 90° by a static mirror $M_1$. A NIR beam (e.g., at 660 nom) passes through a second dichroic mirror ($DM_2$). A flip mirror (FM) is used to switch between the two sources. The beams are focused by lens $L_1$ into a 2 m single mode fiber (SMF) with a 3 μm core. The beam exiting the SMF is focused by side-view optics ($L_2$-$L_4$) and scanned by miniature 3-axis mirror $M_2$ to generate images in either the horizontal or vertical plane. The mirror $M_2$ may be implemented as part of a mirror scanning assembly, in an example embodiment.

Fluorescence is collected by the same optics ($L_2$-$L_4$), descanned by $M_2$, and focused back into the SMF. After transmission, fluorescence is collimated by $L_1$, reflects off either $M_1$, $DM_1$ and $M_3$ or FM, $DM_2$, and $M_4$. Photomultiplier tubes ($PMT_1$) and ($PMT_2$) detect either visible or NIR fluorescence, respectively, that passes through either band pass filter ($BPF_1$) or ($BPF_2$). A high-speed current amplifier may be used to boost the signal, which is digitized by a multi-function data acquisition board that also generates control signals to drive the scanner, and is controlled with custom software.

In terms of the side-view optics and design, in an example embodiment, light exiting the SMF is collimated by lens $L_2$ and focused by $L_3$ (NA=0.25), as shown in FIG. 2A. The focused beam is reflected 90° by $M_2$ into $L_4$ (NA=0.375), resulting in an overall NA=0.38. When $M_2$ rotates about the x-axis and y-axis, the focus moves laterally, as shown in FIG. 2B. When $M_2$ translates in the z-axis, the focus moves in an oblique direction, as shown in FIG. 2C. With $M_2$ at locations +105, 0, and −105 μm in the z-axis, the spot sizes of the Airy disks are 1.51, 1.12, and 1.53 μm, respectively, as shown in FIG. 2D-F. The diffraction limit of 1.19 μm was achieved with $M_2$ at z=0 μm. The focus moves vertically at depths between +90 and -110 μm (200 μm total) and laterally from -101 to +112 μm (213 μm total), as shown in FIG. 2G, thus scanning in an oblique plane. The overall dimension traversed in the oblique plane is 292 μm. Lateral mirror deflections of ±10° and ±8° in the x- and y-axes, respectively, produce a 700×600 μm² FOV in the horizontal plane, see FIG. 2H, and that the combined lateral deflection of ±8° in the X-axis with axial displacement of ±105 μm in the Z-axis produced a 600×292 μm² FOV in the oblique plane, as shown in FIG. 2I. All lenses fit inside a tube with inner diameter (ID) <3.8 mm.

In an example embodiment of the optical probe assembly having the configuration of FIG. 1 and as illustrated in FIGS. 3A-3J, the mirror $M_2$ may be formed as part of a mirror scanning assembly positioned downstream of an optical focusing assembly, such as lens $L_2$ and $L_3$. The lens $L_4$ may be positioned as a collection optical assembly downstream of the mirror and specifically on a side surface of the "housing" (see, FIG. 3I) for side illumination and side viewing. An incident beam from the focusing assembly forms an ellipse on the $M_2$ reflector surface (see, the example implementation of $M_2$ in FIG. 3B labeled as "reflector", able to scan in three dimensions). In an example, when $M_2$ translates in the z-axis, a scan area may be covered with dimensions of 1800 and 1200 μm in the major and minor axes, respectively, as shown schematically in FIG. 3A. In an example, we used this geometry to design a monolithic 3-axis scanning assembly or endomicroscope as shown in FIG. 3B. The scanning assembly includes an inner reflector, reflecting the incident radiation. The scanning assembly includes U-shaped "suspensions" and an "actuator" that moves the reflector in the different 3-axes of movement for scanning. That is, the reflector may be positioned at an angle relative to an axial beam path of an incident radiation to deflect that radiation into a lateral axis for emitting a side of the housing. The scanning assembly may be configured to rotate along a first axis and a second axis for scanning an output beam along a lateral plane and to translate out-of-plane of the first and the second axis for scanning the output beam along an oblique plane, as well.

The frequency response of the mirror scanning assembly maybe determined by the set of "inner" and "outer" multibeam torsional springs. The reflector is mounted on a "gimbal" that rotates about the x-axis and y-axis, as shown in FIGS. 3C and 3D. In other examples, the gimbal is used to rotate about one of these two axes. The gimbal is attached to the U-shaped "suspensions" that act as levers to lift the reflector out-of-plane when driven at resonance, FIG. 3E.

In exemplary embodiments, the housing is sized to receive a single mode fiber ("SMF") at an end for provide illumination beam to the optical scanning assembly and for receiving images (e.g., fluorescent images) from the optical scanning assembly. In other exemplary embodiments, the housing is sized to receive a multi-mode fiber as the illumination beam source. In the illustrated example of FIG. 3I, the housing includes fiber receptacle opposite the scanning head end for receiving a fiber.

In some embodiments, the SMF (or multi-mode fiber) may be coupled to one or more photodetectors configured to receive a radiation from the sample as collected from the optical scanning assembly and used to construct a 2D or 3D image of the sample. For example, fluorescence emitted from the sample in response to illumination by an output beam emitted along the side of the housing may be collected and converted to 2D or 3D images as described in examples herein. The fluorescence emitted from the samples may include visible photons and/or near infrared photons.

In exemplary embodiments, the housing as an outer diameter of 10 mm or below and preferably an outer diameter of 4 mm or less.

Figure 7:
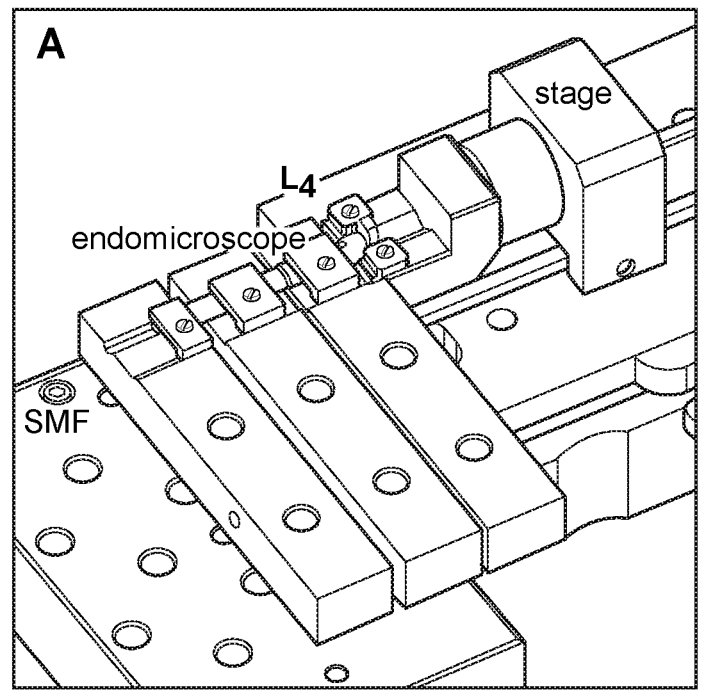
FIG. 7A is a perspective view of an assembly stage for assembling an optical probe assembly, in accordance with an example.
FIG. 7B is a photograph of an assembly stage showing fixtures used to precisely adjust distance between SMF and $L_2$ and between $L_3$ and $L_4$ in the side-view optics.
Figure 7:
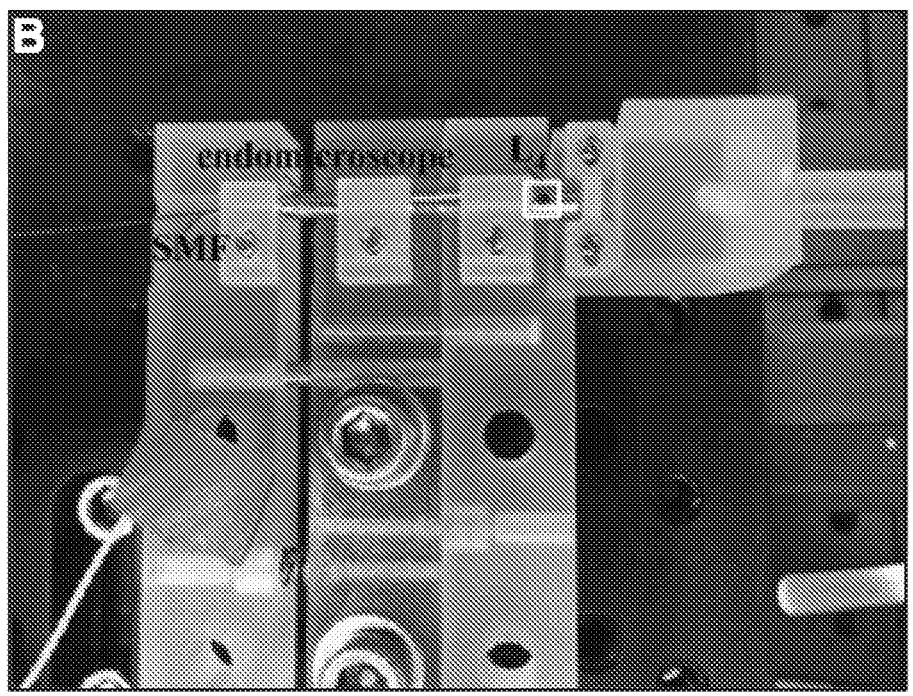

During an example fabrication process, we used alignment fixtures to precisely adjust the distance among individual optical elements, see FIGS. 7A and 7B. We fabricated a chip to support $M_2$ and used copper (Cu) pins connected to aluminum (Al) wires (inset) to deliver drive signals, FIG. 3F. A drawing shows the scanner chip attached to a holder, FIG. 3G, and a schematic of the lateral chip dimensions are provided, FIG. 3H. A drawing and photograph of the assembled instrument are shown in FIGS. 3I and 3J.

The optical scanning probe assembly having a side-view confocal configuration is able to achieve stable scanning and therefore high imaging resolutions. In examples, the imaging resolution is at or 10 μm, at or below 5 μm, at or below 2 μm, or at or below 1 μm.

Figure 2:
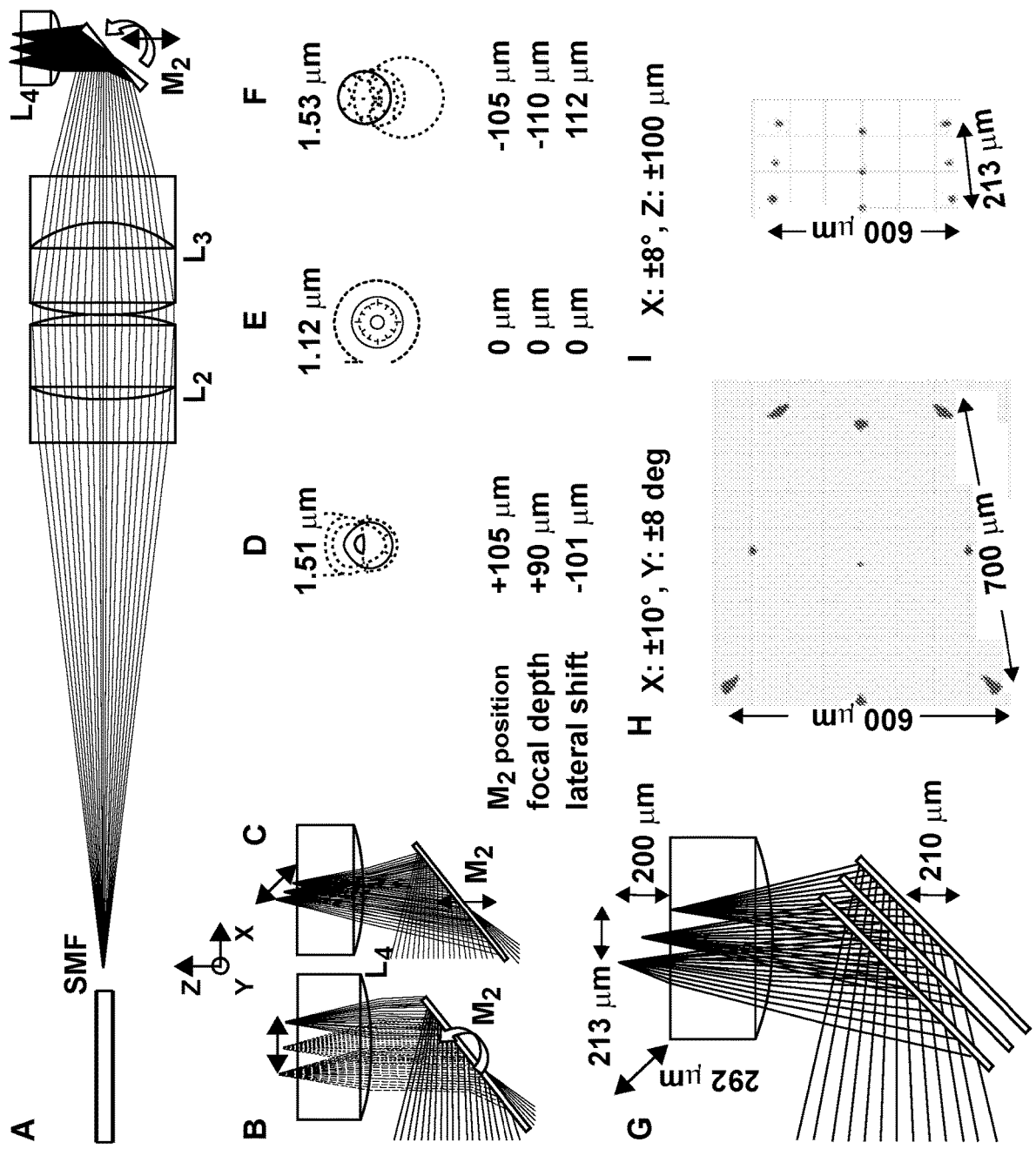
FIG. 2A is a schematic of an excitation beam delivered via the SMF, and passes on-axis through lenses $L_2$-$L_3$ for focusing, in accordance with an example. The 3-axis mirror $M_2$ is located in the post-objective position, and reflects the beam at 90°.
FIG. 2B is a schematic showing that when $M_2$ (of FIG. 2A) rotates about the X- and Y-axes, the focus moves laterally, in an example.
FIG. 2C is a schematic showing that when $M_2$ translates in the Z-axis, the focus moves both axially and laterally along an oblique plane, in an example.
FIGS. 2D-2F illustrate ray trace simulations producing spot sizes of 1.51, 1.12, and 1.53 µm, respectively, with $M_2$ located at +105, 0 and −105 µm in the Z-axis. The focus moves axially to depths of +90, 0 and -110 µm (200 µm) and laterally at -101, 0 and 112 µm (213 µm), resulting in an overall displacement of 292 µm in the oblique plane.
FIG. 2G is a schematic illustration of the lateral and Z-axis changes in focus from different positions linear movements of a mirror, like $M_2$, in accordance with examples.
FIG. 2H is an illustration indicating that ray trace simulations show an expected FOV of 700×600 µm² in the horizontal plane with mirror deflections of ±10° and ±8° in the X- and Y-axes, respectively.
FIG. 2I is an illustration of a projection of the oblique onto the horizontal plane of 600×213 µm² with lateral mirror deflection of ±8° in the X-axes combined with axial displacement of ±100 µm in the Z-axis.
Figure 3:
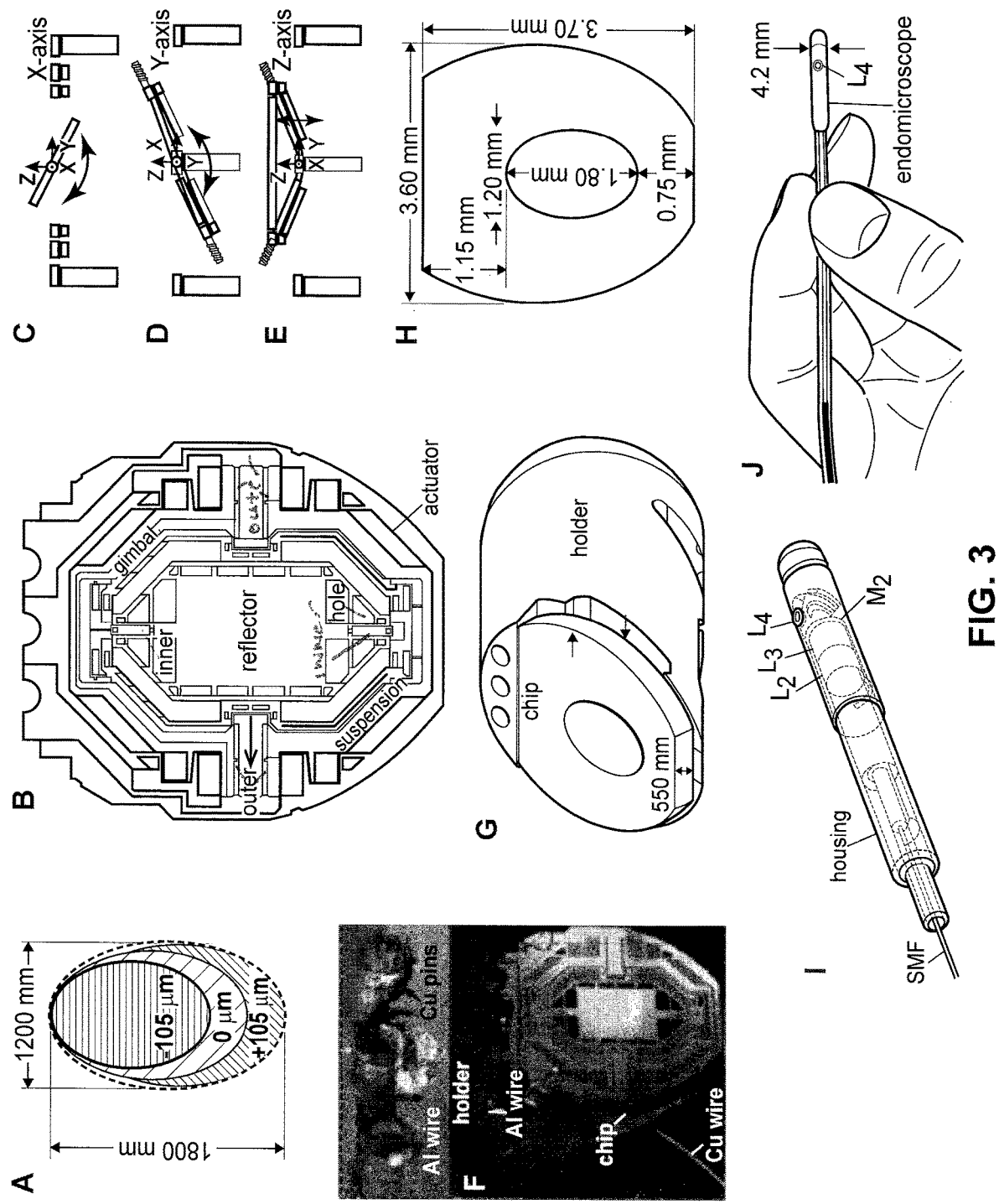
FIG. 3A illustrates ray trace simulations showing an area of an ellipse spanned by an incident beam on a reflector surface with major and minor axes of 1800 and 1200 µm, respectively, when $M_2$ translates axially, in accordance with an example.
FIG. 3B is an illustration of a reflector attached to a gimbal frame driven by electrostatic comb-drive actuators, in accordance with an example. As illustrated in the schematics of FIGS. 3C-3E, the gimbal of FIG. 3B is coupled to inner (FIG. 3C) and outer (FIG. 3D) multi-beam torsional springs and rotates around the X and Y-axes, respectively, in accordance with an example.
As illustrated in FIG. 3E, the gimbal of FIG. 3B is also coupled to U-shaped suspensions that act as levers to displace the reflector out-of-plane in the Z-axis, in accordance with an example.
FIG. 3F is a photograph showing a scanner on a chip for mechanical support and electrical connectivity, in accordance with an example.
FIG. 3G illustrates a chip (550 µm thickness) attached to holder, in accordance with an example. Upper and lower edges (arrows) of the chip show a desire for 100 µm clearance to pass through a stainless-steel tube with an inner diameter (ID) of 3.8 mm, in accordance with an example.
FIG. 3H illustrates lateral dimensions of the chip of FIG. 3G, in accordance with an example.
FIG. 3I illustrates an optical probe scanning assembly, in accordance with an example.
FIG. 3J illustrates the optical probe scanning assembly of FIG. 3I packaged as 4.2 mm diameter side-view endomicroscope, where a flat surface of $L_4$ may be placed in contact with tissue for imaging, in accordance with an example.

In examining the operation of the example optical probe assembly (e.g., confocal endomicroscope) of FIGS. 2 and 3, we applied different sets of drive signals to the scanner to achieve desired image dimensions and frame rates, see Table 1.

|  | imaging plane | frame rate (Hz) | max FOV (μm²) | FOV (pixels) | $f_x$ (kHz) | $f_{y/z}$ (kHz) |
| --- | --- | --- | --- | --- | --- | --- |
| in vivo | horizontal | 10 | 600 × 600 | 400 × 400 | 9.100 | 1.480 |
| in vivo | oblique | 10 | 600 × 292 | 500 × 200 | 9.120 | 1.100 |
| ex vivo | horizontal | 2 | 700 × 600 | 700 × 600 | 9.100 | 1.484 |
| ex vivo | horizontal (zoomed) | 2 | 80 × 80 | 400 × 400 | 9.410 | 1.844 |

Figure 4:
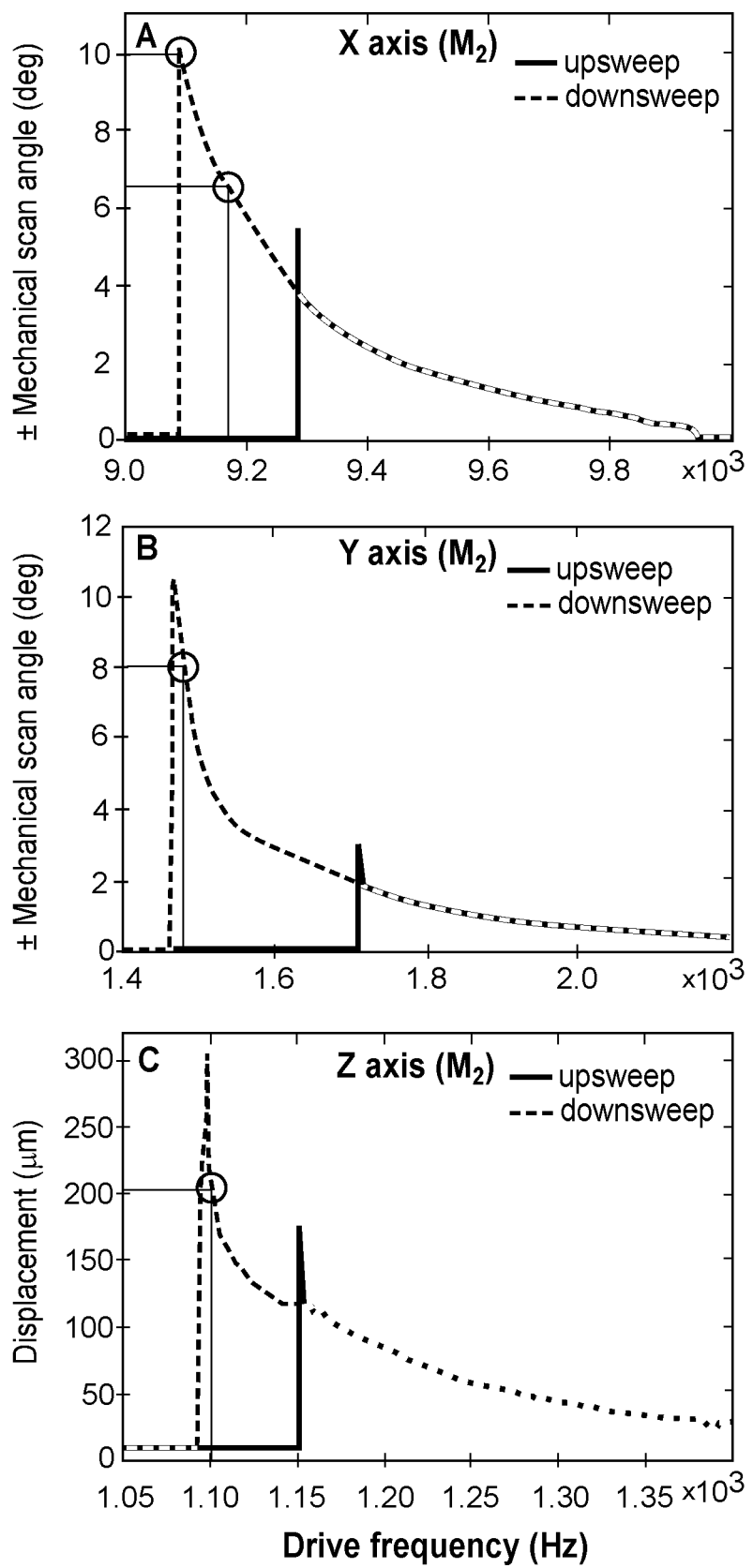
FIGS. 4A-4C are plots of performance of a 3-axis scanner. For the illustrated plots, a drive signal with either an upsweep (low-to-high frequency) or downsweep (high-to-low frequency) to characterize the frequency response of the scanner was used, in the X-axis (FIG. 4A), Y-axis (FIG. 4B), and Z-axis (FIG. 4C). Operating frequencies of $f_X$=9.100 and $f_Y$=1.484 kHz are used for the X- and Y-axes, respectively, to image in the horizontal plane, and $f_X$=9.120 and $f_Z$=1.100 Hz are used for the X- and Z-axes, respectively, to image in the oblique plane. Lateral deflections of ±10° and ±8°, respectively, and axial displacement of ±105 µm are achieved. When $M_2$ is driven in the XZ mode, axial and lateral displacements of 200 and 213 µm are achieved, resulting in images generated in the oblique plane with dimensions of 292 µm.

In an embodiment, we used a downsweep (high-to-low) in drive frequency to achieve the maximum lateral mechanical scan angle greater than ±10° in either the X or Y-axes, as shown in FIGS. 4A and 4B. We also used a downsweep to produce the maximum out-of-plane displacement >300 μm in the Z axis, as shown in FIG. 4C. By adjusting the drive frequency to activate either the tilt or piston mode, we can "switch" the scanner to image in either the horizontal or oblique plane. Using a sine wave at 60 $V_{pp}$, we drove the x- and y-axes at $f_x$=9.100 and $f_y$=1.480 kHz, respectively, to produce mechanical scan angles of ±10° and ±8°, respectively, to achieve a FOV of 600×600 μm² in the horizontal plane for in vivo imaging. We slightly reduced the FOV for faster imaging at 10 frames per sec. We drove the x-axis at $f_x$=9.120 kHz with a sine wave at 60 $V_{pp}$ and the z-axis at $f_z$=1.100 kHz with a square wave at 35% duty cycle and 60 $V_{pp}$ to achieve a FOV of 600×292 μm² in the oblique plane.

Figure 5:
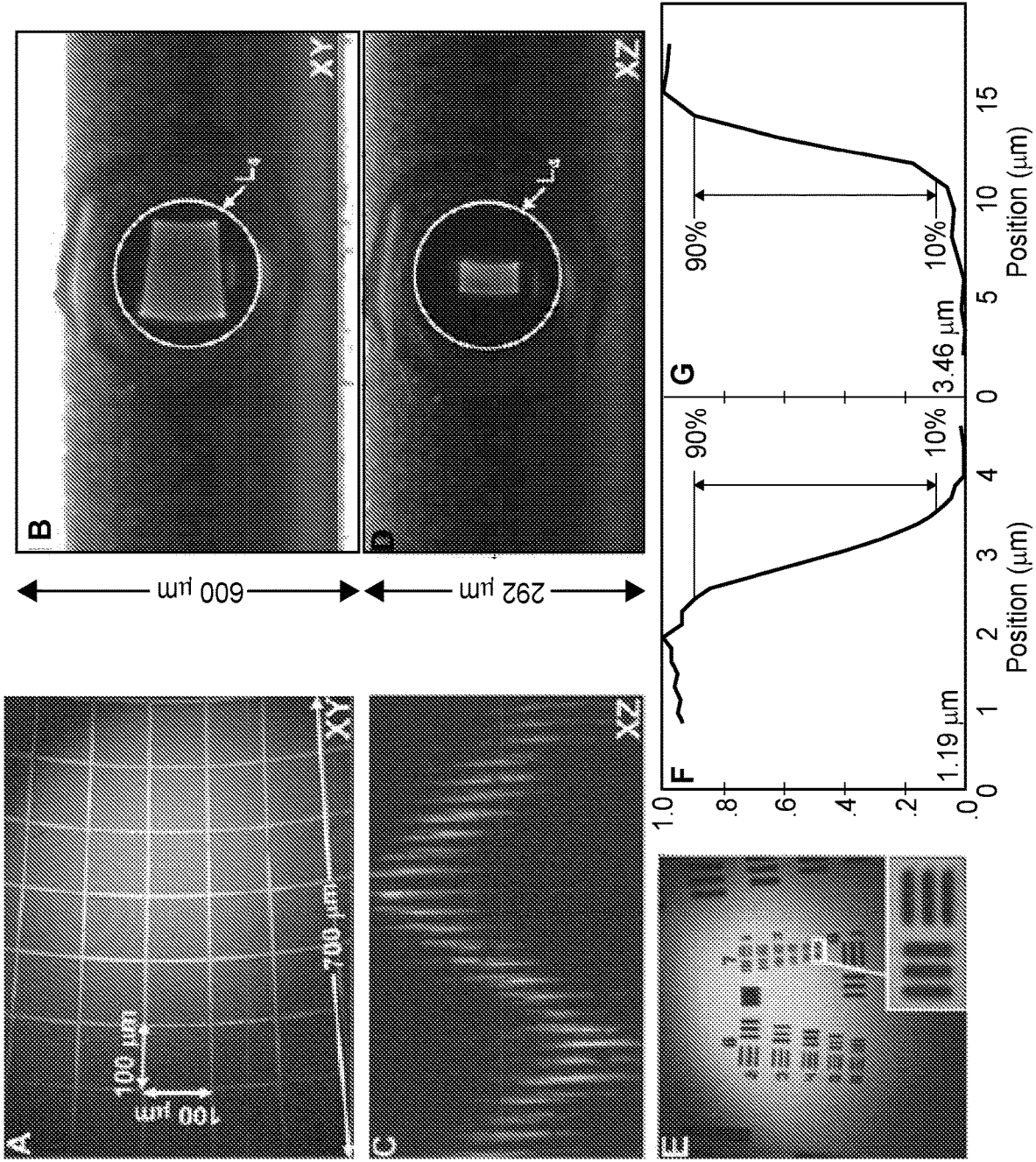
FIGS. 5A-5E illustrate imaging performance an optical probe assembly, in accordance with an example herein.
FIG. 5F illustrates resolution of 1.19 µm in horizontal plane was measured from width of transition from 10% to 90% of maximum intensity from profile across knife-edge target.
FIG. 5G illustrates resolution of 3.46 µm in oblique plane was measured using the same metric.
Figure 8:
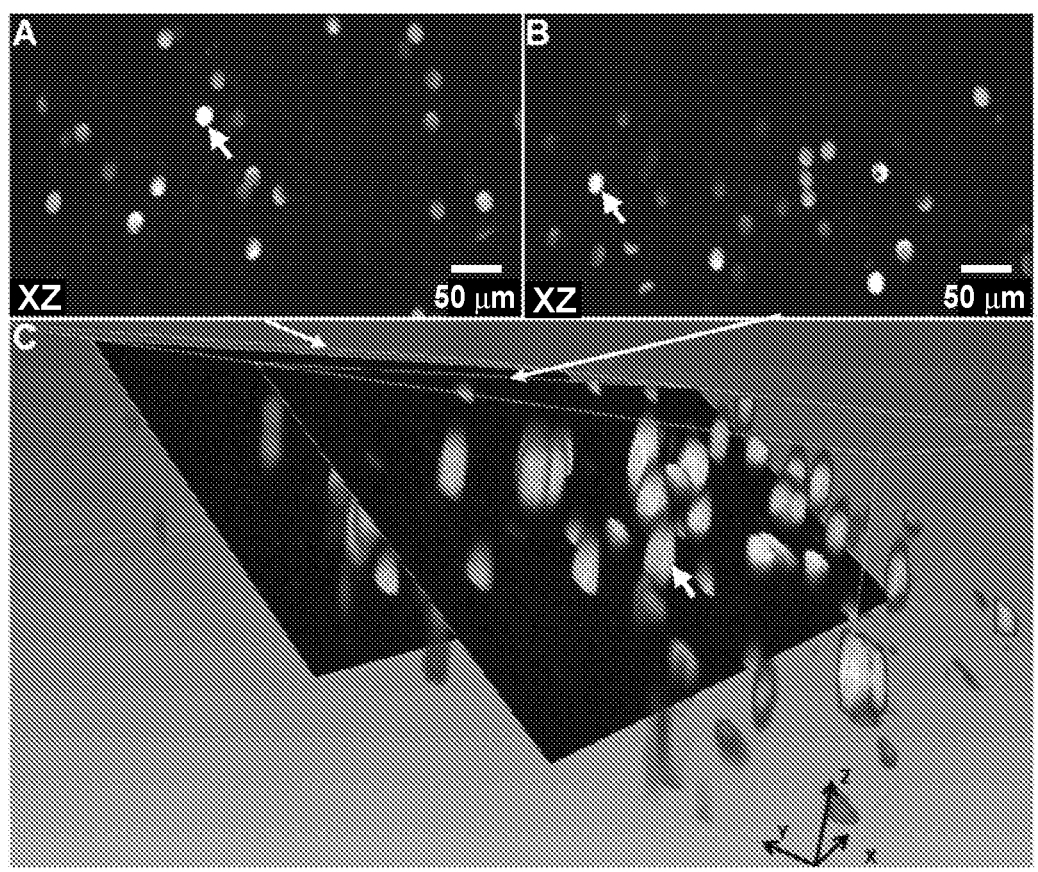
FIGS. 8A and 8B are images of fluorescent phantom imaged using an optical probe assembly and for individual optical sections are collected in the oblique plane from embedded 15 µm diameter fluorescent beads (arrows) using $l_{ex}$=660 nm.
FIG. 8C is a three-dimensional (3D) volumetric images of fluorescent phantom of a stack of oblique images collected combined to construct the 3D volumetric image.

In an example implementation of an optical probe scanning assembly, the performance of a side-view confocal endomicroscope was validated over the full FOV of 700× 600 μm² in the horizontal plane using a grid target consisting of 100×100 μm² boxes, as shown FIG. 5A. The scan pattern can be seen on the flat surface of $L_4$, in FIG. 5B. We confirmed a vertical imaging depth of 200 μm using a microtrench phantom etched in a zig-zag pattern, as shown FIG. 5C. The projection of the scan pattern in the oblique plane on $L_4$ is shown, FIG. 5D. We collected a reflectance image from a standard resolution target in the horizontal plane to qualitatively estimate a lateral resolution of —2 μm, FIG. 5E. Bars from group 7, element 6 are clearly seen (inset). We quantified a lateral resolution of 1.19 μm from the transition width between 10% to 90% of the maximum intensity from a line profile across a knife-edge target, FIG. 5F. We measured a resolution of 3.46 μm in the oblique plane using a similar metric, FIG. 5G. We used this instrument to collect fluorescence images in the oblique plane from a phantom consisting of embedded 15 μm diameter fluorescent beads, FIG. 8A and 8B. A stack of oblique images were combined to form a 3D volumetric image, FIG. 8C.

Figure 6:
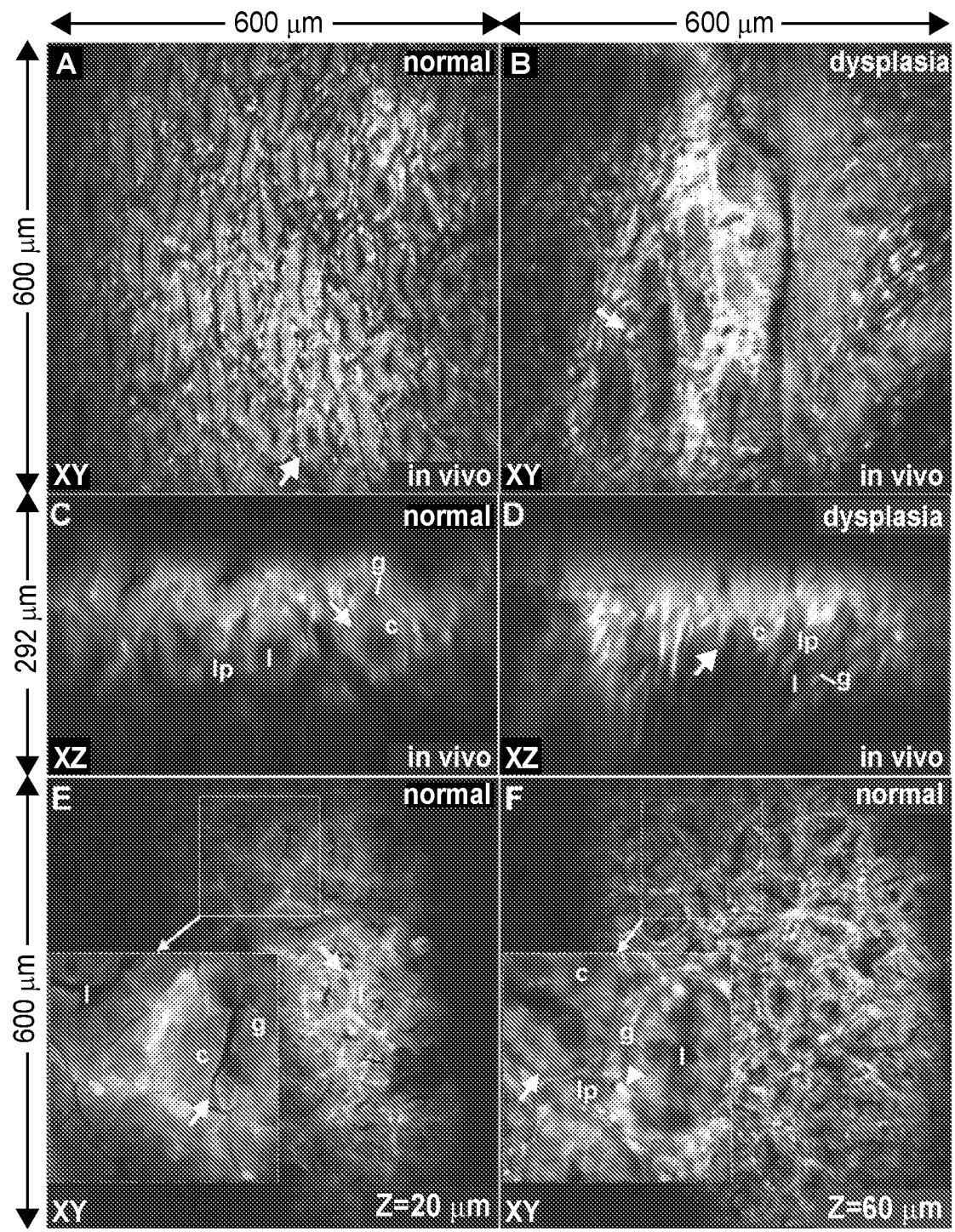
FIGS. 6A-6F are images of mouse colonic epithelium expressing tdTomato, as captured by optical probe assemblies, in accordance with an example. Optical sections were collected in vivo in the horizontal plane at depth of Z=100 µm using $l_{ex}$=561 nm from normal (FIG. 6A) and dysplastic (FIG. 6B) mouse colonic epithelium. Differences in size and morphology of crypt structures (arrows) can be appreciated. Images in the oblique plane from normal (FIG. 6C) and dysplastic (FIG. 6D) colonic epithelium are shown. ROI (inset) with dimensions of 80×80 µm² can be electronically magnified to distinguish individual cells. Differences in epithelial crypt structure were validated ex vivo at depths of Z=20 µm (FIG. 6E) and 60 µm (FIG. 6A). Key: crypt (arrow), lumen (l), goblet cells (g), cytoplasm (c), inflammatory cells (arrowhead), lamina propria (lp).

In an example implementation of an optical probe scanning assembly, the side-view confocal endomicroscope was used to collect confocal fluorescence images in vivo using visible excitation from mouse colonic epithelium that constitutively expresses tdTomato and spontaneously develops adenomas. We could easily maneuver the instrument in mouse colon to accurately position the imaging optics on an epithelial ROI. In the horizontal plane, we visualized well organized crypt structures (arrow) from normal colon, as shown in FIG. 6A. By comparison, dysplastic crypts (arrow) appear enlarged in size and distorted in shape, FIG. 6B. In the oblique plane, normal crypts appear oval in shape and uniform in size, as shown in FIG. 6C, but dysplastic crypts are elongated in shape and variable in dimension, as shown in FIG. 6D. We reduced the frame rate to 2 per sec for ex vivo imaging, and increased the drive voltage to the scanner to electronically magnify ROIs with an area of 80×80 μm² (inset) to clarify epithelial features. We validated crypt structures (arrow) containing goblet cells (g) surrounding a central lumen (l) near the epithelial surface in normal colon (Z=20 μm), FIG. 6E. Fluorescence is seen uniformly in the cytoplasm (c) of individual colonocytes. At greater depths (Z=60 μm), we can clearly identify lamina propria (lp) in gaps between individual crypts and occasional inflammatory cells (arrowheads), FIG. 6F. We also collected images ex vivo from other mouse epithelium, including duodenum and ileum, and identified individual cells, FIGS. 9A and 9B. Images of liver and kidney are also shown to demonstrate the broad applicability of this instrument, FIGS. 9C and 9D.

In an example, we collected fluorescence images ex vivo using NIR excitation following systemically injection of a Cy5.5-labeled peptide specific for EGFR. In the horizontal plane, we visualized minimal staining from normal colonic epithelium, and found crypts to be circular in shape with uniform dimensions, FIG. 10A. Dysplasia showed strong staining, and the crypts were irregular in shape and larger in size, FIG. 10B. In the oblique plane, we saw evenly spaced oval crypts, FIG. 10C, while dysplastic crypts were distorted in architecture and larger in size, FIG. 10D. We combined a stack of oblique images from dysplasia to produce a 3D volumetric image, FIG. 10E.

Figure 9:
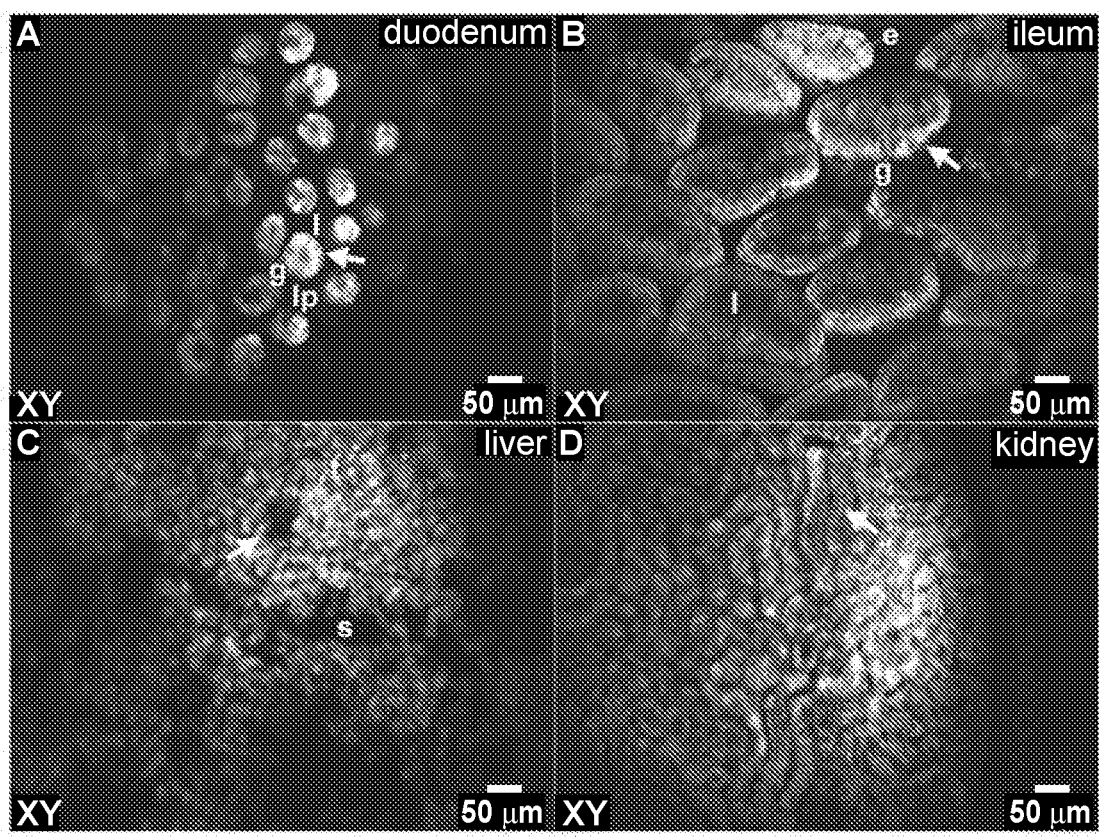
FIGS. 9A-9D are near infrared (NIR) fluorescence images of mouse microanatomy capture by an optical probe assembly, in accordance with an example. The NIR fluorescence images collected ex vivo in the horizontal plane are shown from the epithelium of the duodenum (FIG. 9A), where individual goblet cells (g) are seen surrounding a central lumen (l) within crypt (arrow) structures separated by lamina propria (lp). In the ileum (FIG. 9B), individual enterocytes (e) and goblet cells (g) are seen within the lumen (l) of plica circulari.
Figure 10:
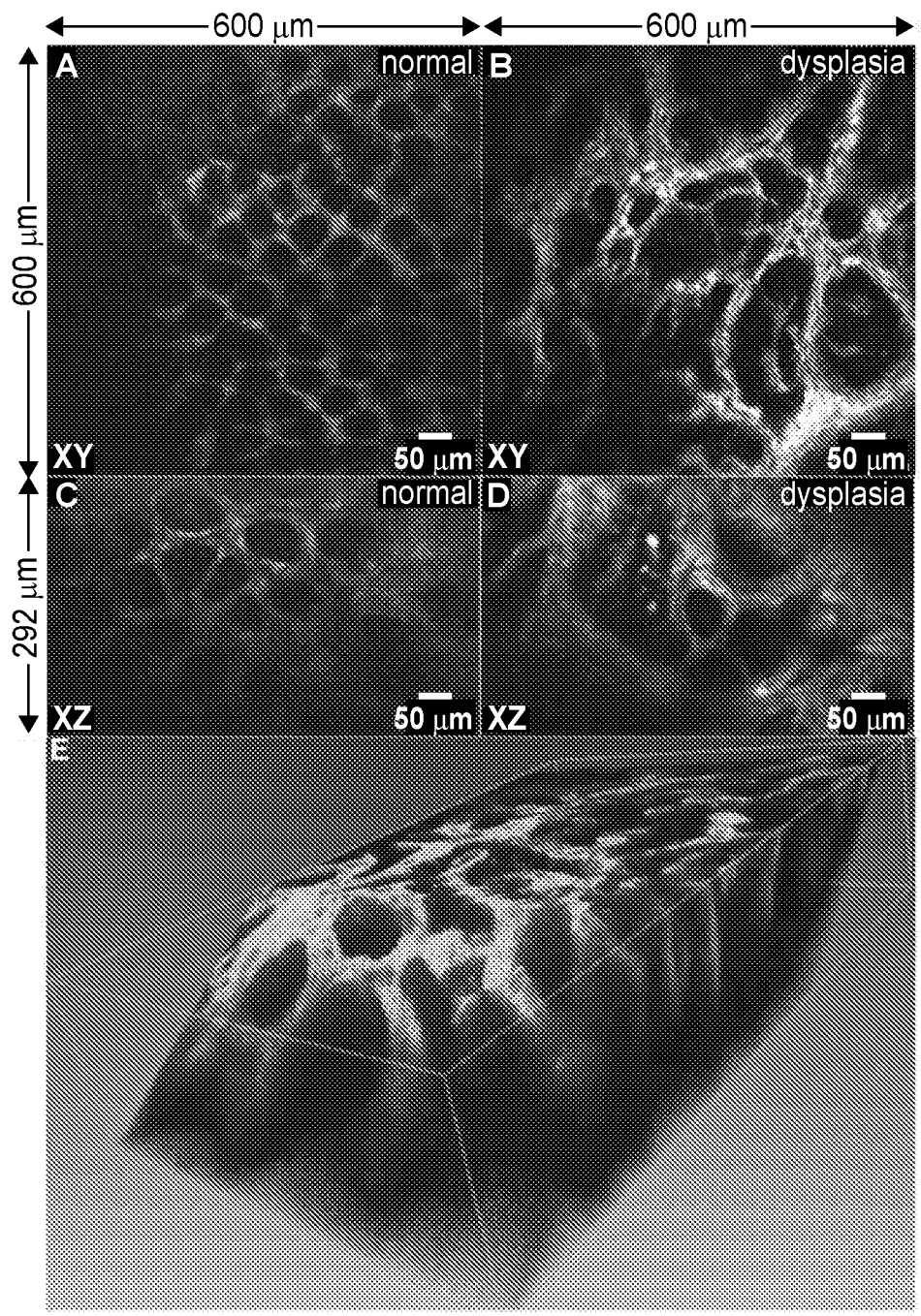
FIGS. 10A-10E are near infrared (NIR) fluorescence images of estimated glomerular filtration rate (EGFR) expression. Fluorescence images are collected from mouse colonic epithelium following systemic injection of a Cy5.5-labeled EGFR peptide. Horizontal images of normal (FIG. 10A) and dysplasia (FIG. 10B) are shown. Oblique images of normal (FIG. 10C) and dysplasia (FIG. 10D) are shown. A 3D volumetric image generated from combining a stack of oblique images collected from dysplasia is shown in FIG. 10D.

The data for FIGS. 9 and 10 was taken from another experiment implementation of an optical probe scanning assembly imaging mice epithelium. Specifically, the side-view confocal endomicroscope was used to perform optical sectioning in colonic epithelium of live animals using visible and NIR excitation to demonstrate the broad use of this instrument. The CPC;Apc mouse is genetically engineered using the Cdx2 promoter to drive a Cre recombinase that sporadically deletes the Apc gene, resulting in spontaneous development of adenomas in the distal colon. The Apc gene is mutated in >80% of human colorectal carcinomas. This mouse was crossed with a wild-type (wt) mouse that has a loxP-flanked STOP cassette to prevent transcription of a downstream tdTomato gene. When the STOP cassette is deleted, tdTomato is expressed constitutively. All experimental procedures were performed in compliance with guidelines of the University of Michigan and were conducted with approval by the University Committee on the Use and Care of Animals (UCUCA).

In this example experiment, we first used visible laser excitation to generate endogenous fluorescence in mouse colonic epithelium from tdTomato. This fluorescent protein has peak absorbance at ~554 nm. We then used NIR excitation to detect exogenous contrast from a Cy5.5-labeled peptide QRHKPRE found to be specific for EGFR. We performed an intra-peritoneal injection of 300 µM of peptide dissolved in 200 mL of PBS via tail vein of CPC;Apc mice. Imaging was performed 1 hour after peptide injection to achieve peak uptake.

During imaging, we first determined the presence and location of adenomas using a white light wide-field endoscope (27030BA, Karl Storz Veterinary Endoscopy). The mice were anesthetized with 2% isoflurane (Fluriso; MWI Veterinary Supply Co). We used the distance between the endoscope tip and the anus and the clockwise location of the adenoma to define landmarks. The angle and extent of insertion were controlled using a translational stage with a rotational fixture to place the optics in direct contact with the lesion. Live video streams were collected at 10 frames per sec. After completion of imaging, the mice were euthanized, and the colon was excised, divided longitudinally, rinsed with PBS to remove debris, and mounted on a glass slide. The tissue was then fixed in 10% buffered formalin and paraffin embedded for routine histology (H&E). The images described in FIGS. 9 and 10 resulted.

The side-view confocal endomicroscopes described herein are example optical probe scanning assemblies and may be used with any illumination source, including visible, infrared, and near infrared (NIR) excitation, thereby allowing the study of a wide range of optical effects (i.e., optical reporters) in tissue. Now, clinical imaging may be performed in small caliber lumens, such as that found in pulmonary bronchioles, biliary tract, and pancreatic duct, due to the size of side-view orientation of the devices described herein.

Further modifications will be apparent from the foregoing and may depend on the particular implementations desired. For example, in vivo imaging speeds can be increased by tuning the multi-beam torsional springs of the scanner gimbal. We have achieved scan speeds of at least 20 frames per sec. Instrument dimensions can be further scaled up or down in size with use of optics that are custom designed and fabricated. Vertical displacements can be adjusted upward by controlling air-damping effects, for example, with the use of a vacuum to reduce the ambient pressure in the scanhead.

One goal is to visualize epithelial cell migration and differentiation in the vertical plane over time and elucidate fundamental mechanisms of cell function and fate. As such, the real-time optical imaging technology may be used to study signals that control important molecular pathways, including immune function, tissue regeneration, and host response, and may substantially accelerate development and evaluation of novel therapies.

Figure 11:
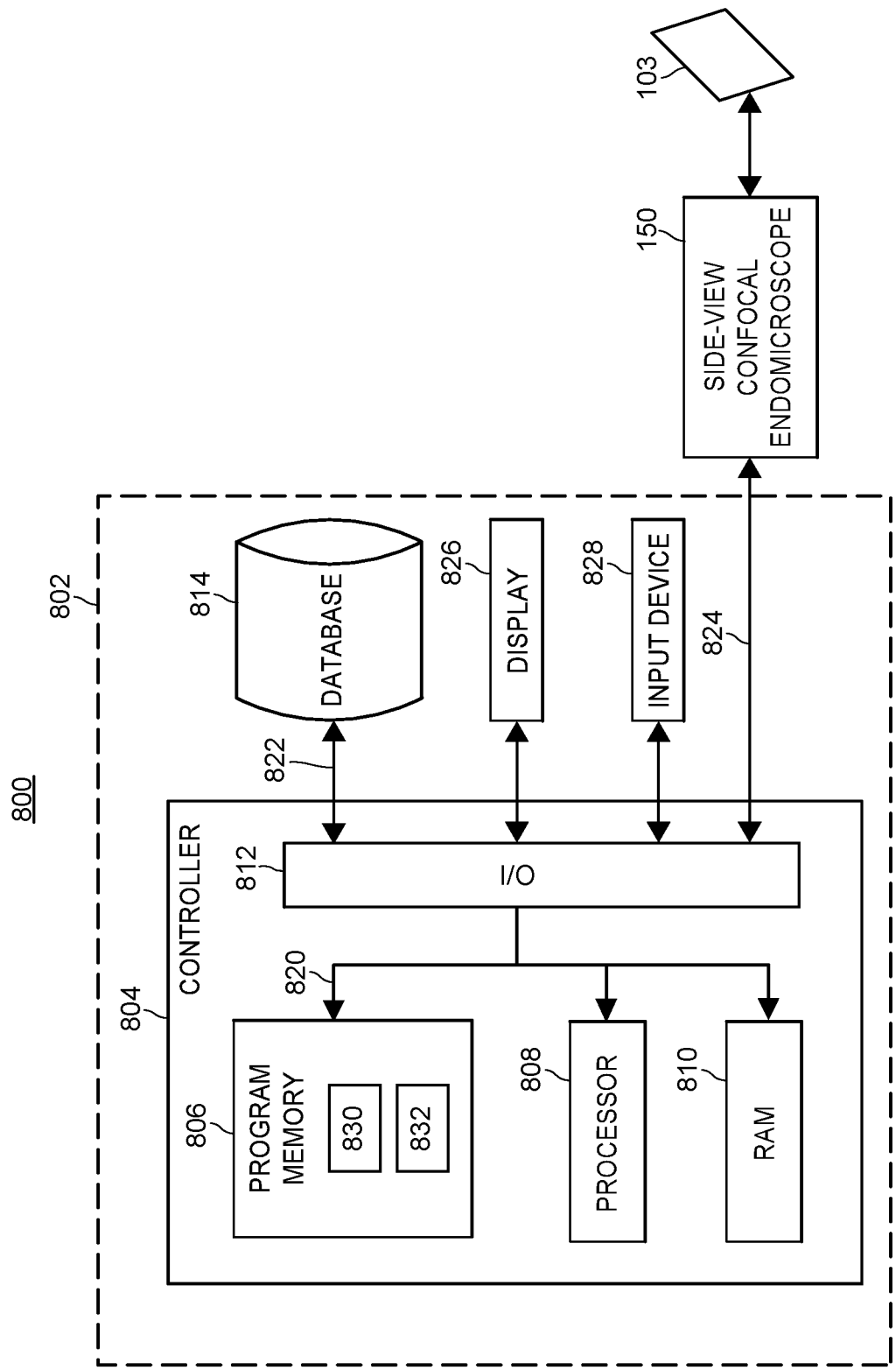
FIG. 11 depicts an example block diagram illustrating various components used in implementing an exemplary embodiment of the side-view confocal endomicroscope, in accordance with various embodiments.

The confocal endomicroscopes herein may be used in a system configuration, an example of which is provided in FIG. 11, which shows an example block diagram 800 showing a scanning device 802. In an example embodiment of an optical probe scanning assembly, a side-view confocal endomicroscope 150 may be positioned within, adjacent, or otherwise coupled to a specimen 103 in accordance with executing the functions of the disclosed embodiments. The scanning device 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, the processor 808 (may be called a microcontroller or a microprocessor), a random-access memory (RAM) 810, and the input/output (I/O) circuit 812, all of which are interconnected via an address/data bus 820. It should be appreciated that although only one microprocessor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824 may operatively connect the controller 804 to the optics 150 through the I/O circuit 812.

The program memory 806 and/or the RAM 810 may store various applications (i.e., machine readable instructions) for execution by the microprocessor 808. For example, an operating system 830 may control the operation of the side-view confocal endomicroscope 150 and provide a user interface to the apparatus to implement the processes described herein. The program memory 806 and/or the RAM 810 may also store a variety of subroutines 832 for accessing specific functions of the scanning device 802 and confocal endomicroscope 150. By way of example, and without limitation, the subroutines 832 may include, among other things: a subroutine for controlling operation of the side-view confocal endomicroscope 150, or other endoscopic device, as described herein; a subroutine for capturing images with the side-view confocal endomicroscope 150 as described herein; a subroutine for switching the imaging mode of the side-view confocal endomicroscope 150 as described herein; a subroutine for capturing images over 3 axes; a subroutine for constructing 3D volumetric images of a ROI from the 3-axis scan images collected; and other subroutines, for example, implementing software keyboard functionality, interfacing with other hardware in the scanning device 802, etc. The program memory 806 and/or the RAM 810 may further store data related to the configuration and/or operation of the side-view confocal endomicroscope 150, and/or related to the operation of one or more subroutines. For example, the data may be data gathered by side-view confocal endomicroscope 150, data determined and/or calculated by the processor 808, etc. In addition to the controller 804, the scanning device 802 may include other hardware resources. The scanning device 802 may also be coupled to various types of input/output hardware such as a visual display 826 and input device(s) 828 (e.g., keypad, keyboard, etc.) to fine tune actuation of the axial and lateral scanners. In an embodiment, the display 826 is touch-sensitive, and may cooperate with a software keyboard routine as one of the software routines 832 to accept user input.

In another example experiment, we showed that claudin-1 overexpression in colon cancer and colon epithelium barrier integrity can be visualized in vivo by the combined application of a side-viewing confocal endomicroscope, i.e., in accordance with the optical scanning probe assembly techniques herein, and claudin-1 target peptide. Claudin-1 is a cell membrane protein expressed on colon epithelial cells, and its integrity determines colon epithelium barrier function. Research has shown that claudin-1 expression level increased in colon cancer cell lines, primary, and metastatic colon cancers in human, which makes it a potential biomarker for colon cancer detection. Moreover, claudin-1 has been identified as a probable target of TCF/LEF signaling, and could also be involved in Wnt and Notch signaling pathways. Altered claudin-1 expression in colon epithelial cells can further damage colon epithelium tight junction structure and function, or interfere with cell signaling pathways to dysregulate tissue homeostasis and promote tumorigenesis. The side-view confocal endomicroscopy techniques herein can be used to visualize the alternation of colon epithelial structure in vivo with histology-like quality. Indeed, the present techniques are particularly suitable for capturing small and early lesions in limited colon luminal space.

For this experiment, we hypothesized that increased claudin-1 expression in colon epithelial cells and dysregulated crypt structure would be visualized after administrating claudin-1 specific peptide in colon adenoma mouse model. We also hypothesized that loss and regaining of colon epithelial junction integrity would be visualized during DSS-induced acute and chronic colitis in vivo.

For experiment conditions, all animal experiments were performed with approval from the University Committee on the Use and Care of Animals (UCUCA) at the University of Michigan. Mice were group housed (2-4/cage), given a standard chow diet and water ad libitum, and exposed to a 12 hours light/12 hours dark circle. Chlorophyll-free chow diet (ENVIGO TD.97184) was provided 1 week prior to imaging to minimize background autofluorescence.

Colonic neoplasia: CPC;Apc mice (CDX2-Cre; $Apc^{580S/+}$) were generated by intercrossing CDX2P 9.5-NLS Cre mice with mice carrying loxP-flanked Apc alleles homozygously (ApcloxP/loxP, 580S). The expression of CDX2P9.5 fragment is throughout the caudal region of embryo and restricted in the terminal ileum, cecum and colon in adult tissues. The CPC; Apc mice express truncated Apc allele in the colon that results in development of spontaneous adenomas as early as 4-6 weeks of age. Colonic inflammation: C57BL/6J mice were obtained directly from Jackson Laboratory. Colitis was induced at 10-12 weeks of age. Acute colitis was induced by adding 2% dextran sulfate salt (DSS) to the drinking water for 5 days. Chronic colitis was induced by adding 2% DSS for 5 days followed by 10 days for recovery over 3 rounds. Mice were imaged after the final 10 day recovery period. Peptide synthesis and characterization: the claudin-1 peptide (RTSPSSR) was synthesized using a PS3 automatic synthesizer (Protein Technologies Inc), and labeled with Cy5.5, a near infrared red (NIR) fluorophore (cyanine5.5 NHS ester, Lumiprobe 27020) at the C-terminus using a GGGSK linker, hereafter RTS*-Cy5.5.[17] A scrambled peptide (SPTSSRR) was used for control, and was also labeled with Cy5.5, hereafter SPT*-Cy5.5. The purity of both peptides was >99% by HPLC. The peptide was lyophilized for storage at −80° C.

Figure 12:
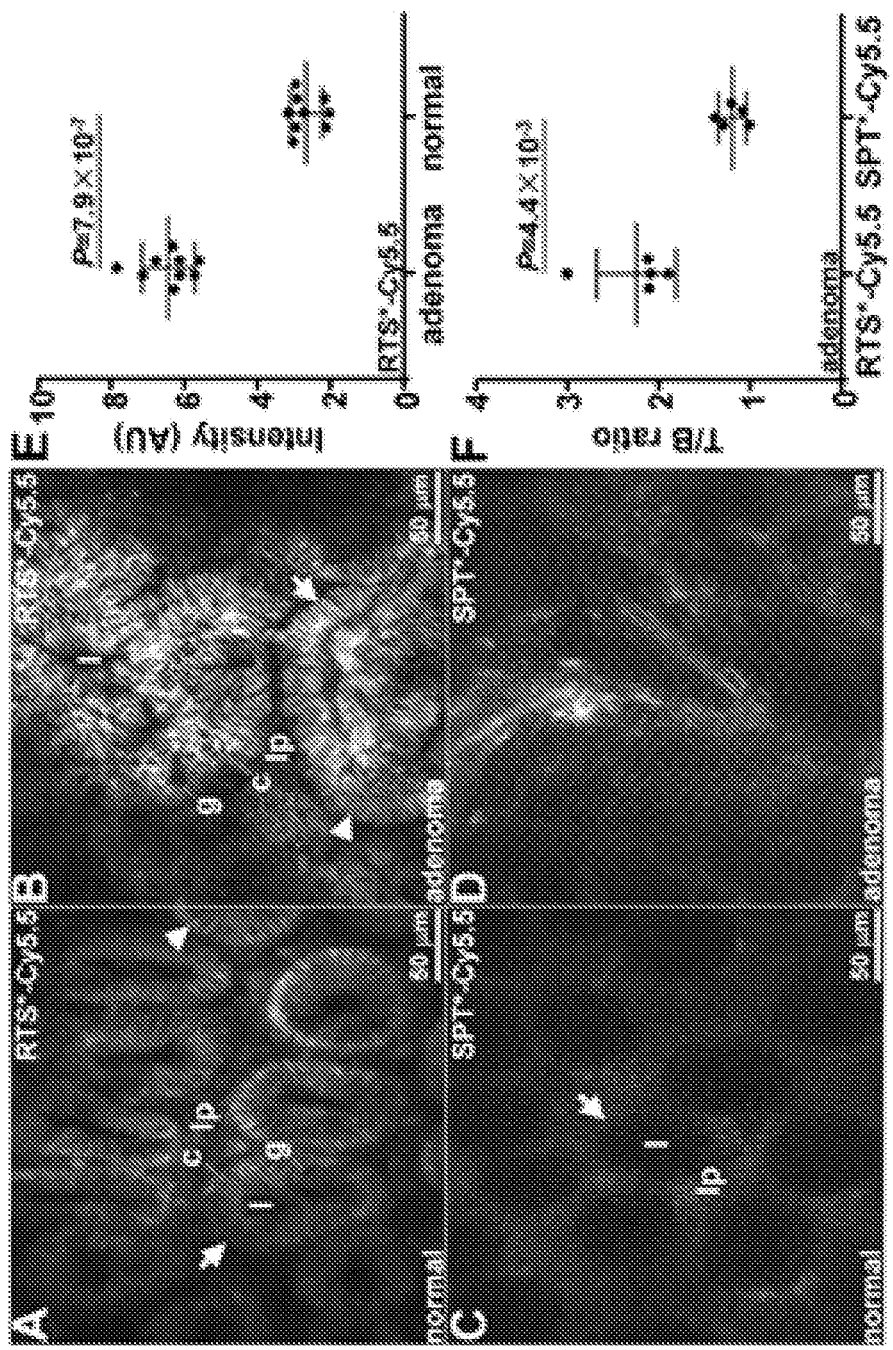
FIGS. 12A-12D are in vivo images from normal (FIG. 12A) colonic mucosa and adenoma (FIG. 12B) mouse colonic epithelium, for 1 hour post-injection of RTS*-Cy5.5 at WD=100 µm. Crypt structures and individual cells can be identified. Images are shown of normal (FIG. 12C) and adenoma (FIG. 12C) following injection of SPT*-Cy5.5 (control).
FIG. 12E illustrates quantified results showing significantly greater mean (±SD) fluorescence intensity for adenoma versus normal with RTS*-Cy5.5 from n=9 mice by paired t-test. Each data point represents the average fluorescence value of 3 independent ROI from one adenoma or adjacent normal tissue.
FIG. 12F illustrates that five mice from FIG. 12E were used for paired SPT*-Cy5.5 imaging. The mean (±SD) T/B ratio for RTS*-Cy5.5 is significantly greater than that for SPT*-Cy5.5 in adenomas by two-sample t-test after log transformation. Key: crypt (arrow), tight junction (arrowhead), lumen (l), colonocytes (c), goblet cells (g), lamina propria (lp).

In an implementation, we imaged for claudin-1 expression in colonic neoplasia, using a side-view confocal endomicroscope, in accordance with the present techniques. That is, an optical scanning probe assembly was used to image claudin-1 expression with sub-cellular resolution following systemic injection of RTS*-Cy5.5. Adenomas were localized using the landmarks identified by wide-field endoscopy. Normal crypt structures (arrow) appear oval in shape with similar dimensions, FIG. 12A. Expression of claudin-l (arrowhead) can be appreciated at tight junctions in between cells. Lamina propria (lp) is seen in between crypts. Individual colonocytes (c) and goblet cells (g) surrounding a central lumen (l) can be identified. By comparison, dysplastic crypts (arrow) show greater intensity, and are much larger in size, elongated in shape, distorted in architecture, and variable in dimension, FIG. 12B. The lamina propria appears crowded. SPT*-Cy5.5 (control) produced a vague appearance of crypt structures (arrow) in normal colon, FIG. 12C, and a non-specific staining pattern in adenoma, FIG. 12D. We quantified these results, and found >2-fold greater intensity from adenoma versus adjacent normal colonic mucosa using RTS*-Cy5.5 at 1 hour, FIG. 12E. The T/B ratio was significantly greater for RTS*-Cy5.5 than for SPT*-Cy5.5 in adenomas at 1 hour, FIG. 12F.

Figure 13:
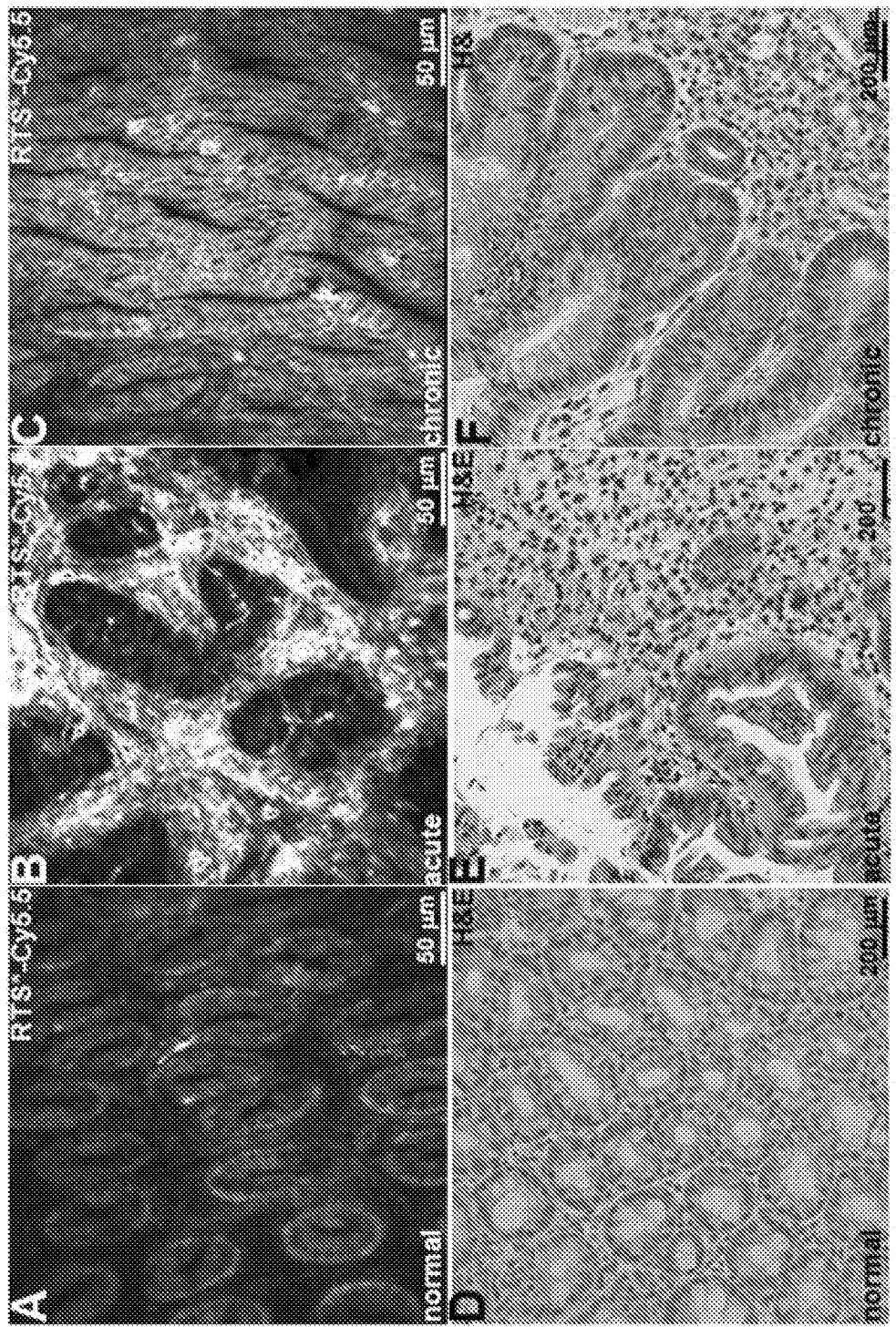
FIGS. 13A-13C are in vivo images taken at 1 hour post-injection of RTS*-Cy5.5 shown for normal crypts (FIG. 13A), after acute inflammation where peptide extravasates into the lamina propria (lp) (FIG. 13B), and after chronic inflammation where crypts regenerate (FIG. 13C).
FIGS. 13D013F illustrate corresponding histology stained H&E (hematoxylin and eosin stain).

In another implementation, we imaged for claudin-1 expression in colonic inflammation, using a side-view confocal endomicroscope, in accordance with the present techniques. That is, an optical scanning probe assembly was used to image claudin-1 expression in vivo in C57BL/6J mice with acute and chronic colitis following systemic injection of RTS*-Cy5.5. Prior to induction of inflammation, RTS*-Cy5.5 staining at the site of tight junctions (arrowhead) was observed in normal crypts, FIG. 13A. Acute colitis was induced by orally administering 2% DSS to the mice each day for 5 days. On in vivo imaging, the crypts appear enlarged, and extravasation of RTS*-Cy5.5 into the lamina propria resulted in intense signal, FIG. 13B. Chronic colitis was induced by administering 2% DSS each day for 5 days followed by 10 days off over a total of 3 rounds. On in vivo imaging, crypt structures showed regenerative features characterized by increased epithelial cell density, enlarged crypt size, and crowded lamina propria, FIG. 13C. Corresponding histology (H&E) for each condition is shown, FIG. 13D-13F. Claudin-1 expression could still be clearly seen at the site of tight junctions (arrowhead) in either condition.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An optical probe scanning assembly comprising:
a housing having a proximal end configured to receive an optical fiber beam source and a distal end for positioning at a sample, the housing having a length that extends along a longitudinal axis extending from the proximal end to the distal end;

an optical focusing assembly configured to focus an output beam, from the fiber beam source, along an axial beam path; and a mirror scanning assembly positioned downstream of the optical focusing assembly in a post-objective position, the mirror scanning assembly being positioned at an angle relative to the axial beam path to deflect the output beam into a lateral axis for emitting the output beam from a side of the housing, the mirror assembly further comprising a reflector positioned centrally within a U-shaped suspension, the reflector configured to rotate along a first axis and a second axis for scanning the output beam along a lateral plane and the U-shaped suspension configured to translate the reflector out-of-plane of the first and the second axis for scanning the output beam along an oblique plane.

2. The scanning assembly of claim 1, wherein the mirror scanning assembly comprises a gimbal assembly connected to the reflector and configured to controllably rotate the reflector about one or more axes for scanning the output beam along the lateral plane.

3. The scanning assembly of claim 2, wherein the gimbal assembly is configured to controllably rotate the reflector about two orthogonal axes for scanning the output beam along the lateral plane.

4. The scanning assembly of claim 1, further comprising a collection optical assembly positioned downstream of the mirror scanning assembly.

5. The scanning assembly of claim 1, wherein the housing is configured to receive a single mode fiber or a multi-mode fiber as the optical beam source.

6. The scanning assembly of claim 1, further comprising one or more photodetectors configured to receive a radiation from the sample.

7. The scanning assembly of claim 6, wherein the radiation is a fluorescence emitted from the sample in response to illumination of the sample by the output beam emitted along the side of the housing.

8. The scanning assembly of claim 7, wherein the fluorescence comprises visible photons or near infrared photons.

9. The scanning assembly of claim 1, wherein the optical focusing assembly and the mirror scanning assembly are configured to emit the output beam from the side of the housing at a field of view of 700×600 µm2 or greater.

10. The scanning assembly of claim 9, wherein the optical focusing assembly and the mirror scanning assembly are configured maintain an imaging resolution below 10 µm.

11. The scanning assembly of claim 9, wherein the optical focusing assembly and the mirror scanning assembly are configured maintain an imaging resolution below 5 µm.

12. The scanning assembly of claim 9, wherein the optical focusing assembly and the mirror scanning assembly are configured maintain an imaging resolution below 2 µm.

13. The scanning assembly of claim 9, wherein the optical focusing assembly and the mirror scanning assembly are configured maintain an imaging resolution below 1 µm.

14. The scanning assembly of claim 1, wherein the housing has a diameter of 10 mm or below.

15. The scanning assembly of claim 1, wherein the housing has a diameter of 4 mm or less.

* * * * *